(12) United States Patent
Barbera-Guillem

(10) Patent No.: US 6,268,350 B1
(45) Date of Patent: Jul. 31, 2001

(54) POLYNUCLEOTIDES FOR INHIBITING METASTASIS AND TUMOR CELL GROWTH

(75) Inventor: Emilio Barbera-Guillem, Powell, OH (US)

(73) Assignee: BioCrystal Ltd., Westerville, OH (US)

( * ) Notice: Subject to any disclaimer, the term of this patent is extended or adjusted under 35 U.S.C. 154(b) by 0 days.

(21) Appl. No.: 09/479,524

(22) Filed: Jan. 7, 2000

Related U.S. Application Data

(63) Continuation-in-part of application No. 09/170,948, filed on Oct. 13, 1998, now abandoned.
(60) Provisional application No. 60/062,733, filed on Oct. 23, 1997.

(51) Int. Cl.$^7$ .......................... A61K 48/00; C07H 21/02; C07H 21/04
(52) U.S. Cl. .......................... 514/44; 536/23.5; 536/24.5; 536/23.1
(58) Field of Search ............................... 514/44; 435/328, 435/69.1; 536/23.1, 23.5, 23.4, 24.5

(56) References Cited

U.S. PATENT DOCUMENTS 5,858,990 * 1/1999 Walsh ...................................... 514/44

OTHER PUBLICATIONS

O'Connell et al., "The Fas counterattack: Fas–mediated T cell killing by colon cancer cells expressing FasL", 1996, Journal of Experimental Medicine, vol. 184: 1075–1082.

Turley et al., "Vitamin E succinate induces Fas–mediated apoptosis in estrogen receptor–negative human breast cancer cells", 1997, Cancer Research, vol. 57:881–890.

Lee et al., "The Fas system is a key relator of germ cell apoptoss in the testis", 1997, Endocrinology, vol. 138:2081–2088.

Uhlmann et al., "Antisense Oligonucleotides: A New Therapeutic Principles." Chemical Reviews, vol. 90 (4): 544–584, Jun. 1990.*

Hofmann et al., "Death of Solid Tumor Cells Induced by Fas Ligand Expressing Primary Myoblasts." Somatic Cell and Molecular Genetics, vol. 23 (4): 249–257, 1997.*

Shimizu et al., "A trial to kill tumor cells through Fas (CD95)–Mediated Apoptosis in Vivo." Biochemical and Biophysical Research Communications, vol. 228: 375–379, 1996.*

Stein et al., "Antisense Oligonucleotides as Therapeutic Agents—Is the Bullet Really Magical?" Science, vol. 261: 1004–1012, Aug. 1993.*

Patzel et al., "Theoretical design of antisense RNA structures substantially improves annealing kinetics and efficacy in human cells." Nature Biotech., vol. 16: 64–68, Jan. 1998.*

Drozdzik et al., "Antitumor effect allogenic fibroblasts engineered to express Fas Ligand (FasL)." Gene Therapy, vol. 5: 1622–1630, 1998.*

Ledley, F., "Pharmaceutical Approach to Somatic Gene Therapy." Pharmaceutical Research, vol. 13: 1595–1613, Nov. 1996.*

Miller et al., "Targeted vectors for gene therapy." FASEB Journal, vol. 9: 190–199, Feb. 1995.*

* cited by examiner

*Primary Examiner*—Karen M. Hauda
*Assistant Examiner*—Ram R. Shukla
(74) *Attorney, Agent, or Firm*—M. Bud Nelson

(57) ABSTRACT

Provided are one or more polynucleotides, and a method for inhibiting tumor progression in an individual comprising administering to the individual a therapeutically effective amount of the one or more polynucleotides. The one or more polynucleotides comprise FasL sense polynucleotide, or FasL antisense, or a combination thereof.

10 Claims, 4 Drawing Sheets

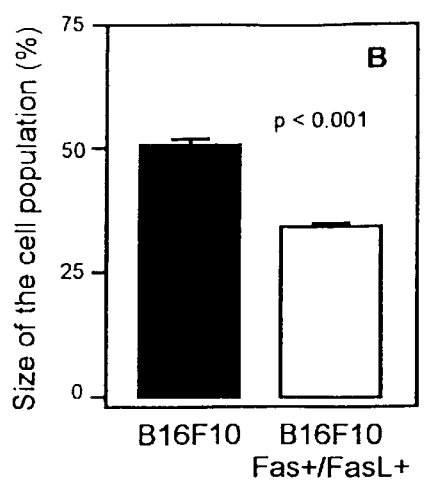
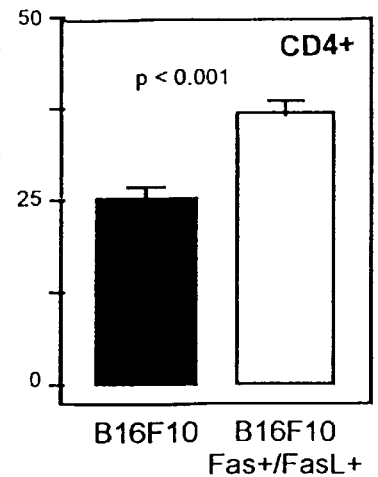
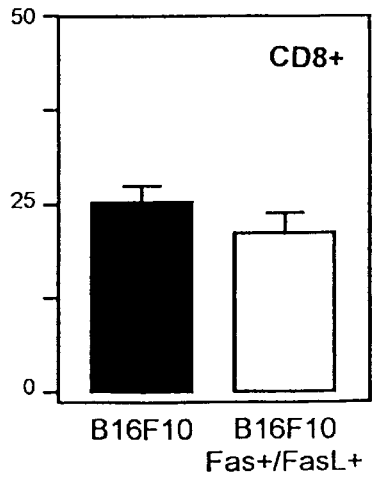
FIG. 5A  FIG. 5B  FIG. 5C
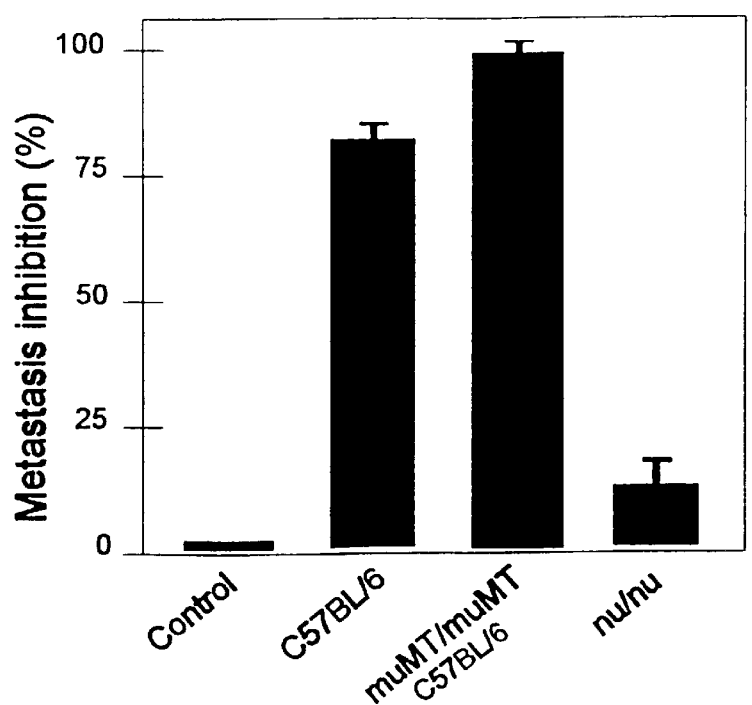
FIG. 6

POLYNUCLEOTIDES FOR INHIBITING METASTASIS AND TUMOR CELL GROWTH

This is a continuation-in-part application based on earlier application Ser. No. 09/170,948 filed Oct. 13, 1998 (now abandoned) which is a nonprovisional application based on Ser. No. 60/062,733, filed Oct. 23, 1997 which are herein incorporated by reference.

FIELD OF THE INVENTION

The present invention is related to novel methods and compositions for anticancer therapy of certain tumor types in humans. More particularly, the present invention is related to the methods for impairing or inhibiting metastasis and tumor cell growth with polynucleotides.

BACKGROUND OF THE INVENTION

Apoptosis is a characteristic form of cell death involving activation of one or more internally controlled pathways leading to autodigestion. Apoptosis can be induced by the binding and cross-linking of a cell surface receptor known as Fas. Human Fas (also known as APO-1 and CD95) is a cell surface protein consisting of 325 amino acids with a signal sequence at the $NH_2$-terminus and a membrane spanning region in the middle of the molecule. Fas appears to be constitutively expressed on cells of a varied, but limited, number of normal tissues, including skeletal muscle, liver, skin, heart, lung, kidney, reproductive tissues, neutrophils and macrophages. Malignant cells of hematologic or non-hematologic origin have also been demonstrated to express Fas (see, e.g., Leithauser et al., 1993, *Laboratory Invest.* 69:415).

Fas-mediated apoptosis (also known as Fas-mediated cytotoxicity) requires cross-linking of Fas with either agonistic anti-Fas antibody, with cell bound FasL (Fas-ligand), or with soluble FasL (see, e.g. Alderson et al., 1995, *J. Exp. Med.* 181: 71–77). FasL is a type II transmembrane protein of the tumor necrosis factor family. Depending on the tumor type, FasL cell surface expression is variable; e.g., detectable in some tumors and absent in others. For those tumors expressing FasL, it has been suggested that such expression provides a mechanism of immune privilege of the tumors; i.e. a means by which the tumor evades immune-induced tumor cell depletion (Walker et al., 1997 *J. Immunol.* 158:4521–4). For example, FasL+ hepatocellular carcinomas were shown to kill Fas+ T lymphocytic cells in coculture (Strand et al., 1996, *Nat. Med.* 2:1361–6); FasL+ human colonic adenocarcinoma cell lines induced apoptosis of Fas+ T lymphocytic cells in coculture (SW480, Shiraki et al., 1997, *Proc. Natl. Acad. Sci. USA* 94:6420–5; SW620, O'Connell et al., 1996, *J. Exp. Med.* 184:1075–82); FasL+ human lung carcinoma cell lines killed Fas+ T lymphocytic cells in coculture (Niehans et al., 1997, *Cancer Res.* 57:1361–6); and FasL+ melanoma cells induced apoptosis of Fas+ target cells in coculture (Hahne et al., 1996, *Science* 274:1363–6). These data suggest that FasL expression by tumor cells enhances tumorigenesis by killing Fas expressing immune effector cells (e.g., activated or tumor-reactive T cells) and surrounding Fas expressing tissue cells (e.g., hepatocytes; see Shiraki et al., 1997, supra). Further, cancer cells found to be FasL+ and Fas+ fail to undergo Fas-mediated apoptosis after treatment with agonistic anti-Fas antibody (O'Connell et al., 1996, supra) suggesting that tumor-expressed Fas did not transmit an apoptotic signal. Resistance to Fas-mediated apoptosis after anti-Fas antibody treatment has also been observed in nonhematopoietic tumors (Owen-Schaub et al., 1994, *Cancer Res.* 54:1580–1586), human hepatoma cells (Ni et al., 1994, *Exp. Cell Res.* 215:332–7), breast carcinoma (Keane et al., 1996, *Cancer Res.* 56:4791–8). Thus, that tumor cells (e.g., from breast, colon, testis, and liver) expressing Fas appear to have lost their sensitivity to anti-Fas mediated cytotoxicity, suggests that tumor cells escape the normal induction of apoptosis that occurs in these tissues (Micheau et al., 1997, *J. Natl. Cancer Inst.* 89:783–789).

A need still exists for a method to impair or inhibit metastasis and tumor cell growth, and with less systemic toxicity than the current standard treatments comprising chemotherapy and/or radiation therapy.

SUMMARY OF THE INVENTION

Accordingly, it is a primary object of the present invention to provide a composition comprising one or more polynucleotides for treating individuals having solid, nonlymphoid tumor.

It is another primary object of the present invention to provide methods for treating individuals having solid, nonlymphoid tumor by administering a composition comprising a therapeutically effective amount of one or more polynucleotides.

It is another primary object of the present invention to provide compositions comprising polynucleotides for treating individuals having solid, nonlymphoid tumor; wherein the compositions comprise antisense to FasL, one or more sense polynucleotides encoding FasL, or a combination thereof.

It is another primary object of the present invention to provide methods for treating individuals having solid, nonlymphoid tumor by administering a therapeutically effective amount of a composition comprising one or more polynucleotides; wherein the composition comprises an antisense to FasL, one or more sense polynucleotides encoding FasL, or a combination thereof.

It is another object of the present invention to provide methods for treating an individual having solid, nonlymphoid tumor comprising FasL(−) tumors by administering a therapeutically effective amount of sense polynucleotide encoding FasL in inducing the expression of Fas ligand (FasL) in FasL(−) tumor cells, which can impair or inhibit metastasis and tumor cell growth.

It is another object of the present invention to provide a method for treating individuals having FasL(−) tumors, wherein the method comprises administering a therapeutically effective amount of sense polynucleotide encoding FasL in inducing FasL expression in nonadherent FasL(−) tumor.

It is another object of the present invention to provide a method for impairing metastasis in individuals having FasL (−) tumors by administering a therapeutically effective amount of sense polynucleotide encoding FasL in inducing FasL expression in nonadherent tumor cells, and wherein the method is facilitated, at least in part, by Fas-mediated cytotoxicity of the tumor and by Fas-mediated cytotoxicity of tumor promoting B cells local or regional to the tumor.

It is another object of the present invention to provide a method for impairing tumor growth and/or metastasis in individuals having solid, nonlymphoid tumor, wherein the method is facilitated, at least in part, by inhibiting FasL expression in FasL-expressing cells local or regional to the tumor.

The foregoing objects are based on the novel discoveries that metastatic cells and nonadherent tumor cells (under non-anchorage conditions) which are Fas-expressing ("Fas+") can be induced to apoptosis by contact with FasL+ tumor cells; and that inducing FasL expression on FasL(−) tumor cells does not confer immune privilege to these cells in vivo, but instead targets the tumor cells for destruction. Additionally, as disclosed by the present inventor (see, e.g., Barbera-Guillem et al., 2000, *Cancer Immunol. Immunother.* 48:541–549, herein incorporated by reference), B lymphocytes exposed to shed tumor antigen can promote tumor progression. FasL+ tumors can contact and induce cytotoxicity of these Fas+ tumor-promoting B cells. Also disclosed herein is the discovery that by introducing a therapeutically effective amount of a composition comprising polynucleotide comprising FasL anti-sense in an area local or regional to a tumor, tumor growth and/or metastasis is inhibited. Additionally, disclosed herein is the discovery that administration of a therapeutically effective amount of a composition comprising one or more polynucleotides in an area local or regional to a tumor can effect an inhibition of tumor growth and/or metastasis. For example, such a composition comprises a combination of one or more polynucleotides comprising antisense to FasL, and one or more sense polynucleotides encoding FasL.

These and further features and advantages of the invention will be better understood from the description of the preferred embodiments when considered in relation to the figures in which:

BRIEF DESCRIPTION OF THE DRAWINGS

FIG. 5 are bar graphs illustrating, in mice injected with either B16F10 cells or Fas+/FasL+ B16 cells, relative populations of B cells (FIG. 5A), CD4 cells (FIG. 5B), and CD8 cells (FIG. 5C).

FIG. 6 is a bar graph illustrating metastasis inhibition by a control group, C57BL/6 mice, muMT/muMT C57BL/6 mice, and nu/nu mice.

DETAILED DESCRIPTION OF THE PREFERRED EMBODIMENTS

Definitions

Figure 1:
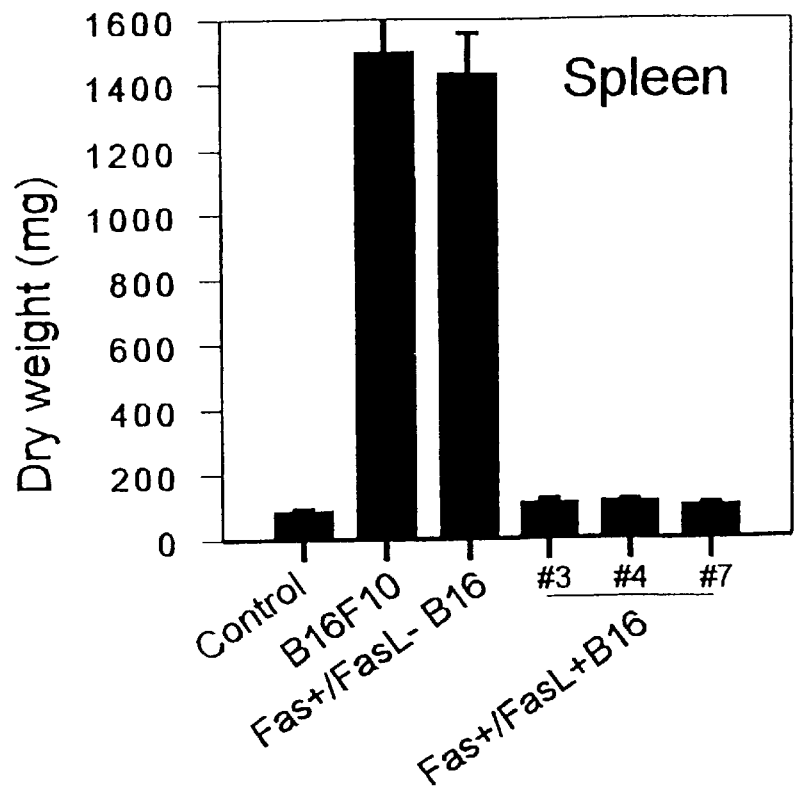
FIG. 1 is a bar graph illustrating tumor growth (as measured by spleen weight) in mice injected with B16F10 cells ("B16F10"); or Fas+/FasL− B16 cells; or PBS injection; or Fas+/FasL+ B16 clones #3, #4, and #7.

The term "metastases" or "metastatic tumor cell" is used herein, for purposes of the specification and claims, to mean a metastasis from a primary tumor wherein the primary tumor is a solid, non-lymphoid tumor, as will be more apparent from the following embodiments. In a preferred embodiment, the metastases are Fas+.

The terms "solid, non-lymphoid tumor" or "tumor" are used hereinafter, for purposes of the specification and claims, to mean any primary tumor of nonhematopoietic and ductal epithelial cell origin, including, but not limited to, tumors originating in the liver, lung, brain, lymph node, bone marrow, adrenal gland, breast, colon, pancreas, stomach, or reproductive tract (cervix, ovaries, endometrium etc.). In a preferred embodiment, the tumor is Fas+.

The term "nonadherent tumor cells" is used herein, for purposes of the specification and claims, to mean a metastatic tumor cell such as may be found moving through tissues of a body; a tumor cell circulating in blood, lymph or other body fluids; a tumor cell having a high potential to metastasize (e.g., expressing IL-2Rα as described in more detail in U.S. Pat. No. 5,536,642); or a solid, non-lymphoid tumor cell which is non-adherent as existing in non-anchorage conditions in a tissue environment. This includes tumor cells growing in clusters without visible intercellular connective matrix or desmoplastic or angiogenic processes, such as exhibited by metastatic growth in the lymphatic sinuses. Non-anchorage conditions, for example, exist during lung metastases formation during cell arrest, and at some points in colony formation. Such tumor cells are nonadherent at points when they circulate freely in the blood or lymph systems.

The term "individual" is used herein, for purposes of the specification and claims, to mean a mammal; and preferably a human, including an individual having a primary tumor comprising a solid, non-lymphoid tumor and/or its metastases, or an individual who has been treated for a solid, nonlymphoid tumor and thereby inherently carries a risk of recurrence because of circulating tumor cells. In either case, the individual is at risk for developing, or has developed, a pro-tumor immune response. In one embodiment of the method and compositions according to the present invention, inducing FasL expression in FasL(−) solid, non-lymphoid tumors may target, contact, and induce Fas-mediated cytotoxicity in, B cells localized in lymphoid tissues regional and/or infiltrating a solid, nonlymphoid in such an individual.

The term "antisense" is used herein in reference to FasL, for purposes of the specification and claims, an to mean an oligonucleotide, modified oligonucleotide (e.g., containing one or more modified bases or synthetic nucleotides), nucleic acid molecule, other nucleotide-containing composition, or an oligomer large enough to be termed a polynucleotide, that binds in a sequence specific manner to a nucleic acid molecule encoding FasL in inhibiting or reducing the expression of FasL from that bound nucleic acid molecule. In a preferred embodiment, the antisense comprises a nucleic acid sequence which comprises 10 or more contiguous nucleotides of SEQ ID NO:7, and which functions to inhibit or reduce the expression of FasL. A preferred FasL antisense may be used to the exclusion of FasL antisense other than the preferred FasL antisense.

The term "FasL negative" or "FasL(−)" is used herein for purposes of the specification and claims, to mean solid, non-lymphoid tumor cells, and particularly nonadherent tumor cells thereof, which lack detectable expression of FasL either on the surface of the cell or at the mRNA level, as determined within the limits of detection by methods conventionally used by those skilled in the art to detect FasL expression including, but not limited to, RT-PCR, immunohistochemical staining, immunofluorescence flow cytometry, and functional bioassays, as will be more apparent from the following embodiments.

The term "FasL positive" or "FasL+" is used herein for purposes of the specification and claims, to mean solid, non-lymphoid tumor cells, particularly nonadherent tumor cells thereof, having detectable expression of FasL on the surface of the cell, as determined by methods conventionally used by those skilled in the art to detect FasL expression including, but not limited to, RT-PCR, immunohistochemical staining, immuno-fluorescence flow cytometry, and functional bioassays, as will be more apparent from the following embodiments.

The term "polynucleotide" is used herein for purposes of the specification and claims, to mean a nucleic acid molecule which may be used by itself (e.g., "naked"), or may further comprise a vector (e.g., for expression), as will be more apparent from the following embodiments. The nucleic acid molecule may comprise nucleotides, one or more nucleotides that contain modifications known to those skilled in the art (e.g., in one or more bases, one or more sugar moieties, one or more internucleotide linkages, one or more backbone modifications, and a combination thereof), or a combination thereof.

The term "vector" or "expression vector" is used herein for purposes of the specification and claims, to mean vectors used in accordance with the present invention as a vehicle for introducing into and expressing in a mammalian cell a gene encoding FasL (for the sense construct), or antisense to FasL. As known to those skilled in the art, such vectors can be selected from plasmids, viruses, and retroviruses. For a recent review of vectors useful in gene therapy of cancer, see Weichselbaum and Kufe (1997, *Lancet*, 349:S10–S12). The features of a vector which make it useful in the methods of the present invention include that it have a selection marker for identifying vector which has inserted therein the desired polynucleotide; restriction sites to facilitate cloning of the desired polynucleotide; and the ability to enter and/or replicate in mammalian cells. In a one embodiment wherein inserted is a FasL encoding sequence, the vector may further comprise an activation-inducible cis-acting regulatory element for upregulating FasL expression (Egr-3; SEQ ID NO:16 see, e.g., Mittelstadt and Ashwell, 1998, *Mol. Cell. Biol.* 18:3744–3751), wherein the regulatory element is operatively linked to the gene encoding FasL in a manner permitting upregulation (for example, Egr-3 can be located approximately 200 bp upstream of initiation codon). Examples of a preferred vector for the in vivo introduction of a recombinant vector into mammalian cells include, but are not limited to viral vectors. Virus-based vectors are one preferred vehicle as they infect cells in vivo, wherein during the infection process the viral genetic material is transferred into the cells. A retroviral vector, such as a plasmid containing AAV (Adeno-associated virus) sequences, has been described previously (see for example Chatterjee et al., 1992, *Science*, 258:1485–1488; U.S. Pat. No. 5,252,479, herein incorporated by reference). In one embodiment, the AAV vector contains inverted terminal repeats (ITR) with a selection marker such as the gene encoding neomycin resistance, an SV40 promoter, a polylinker, and other plasmid sequences. A promoter in the ITR drives the expression of the neomycin phos-photransferase gene, whereas the SV40 promoter drives expression of the operably linked FasL gene to be expressed. The inverted terminal repeats of the AAV vector provide a means for integrating the vector, and sequences inserted therein, into the chromosome as the repeats serve as a sequence which has been shown to insert site-specifically, rather than randomly, into chromosomes. Examples of other vectors for the in vitro or in vivo introduction into mammalian cells include retroviral vectors (Miller et al., 1989, *BioTechniques* 7:980–990; Korman et al., 1987, *Proc. Natl. Acad. Sci. USA* 84:2150–54), papovavirus episomes (U.S. Pat. No. 5,624,820, herein incorporated by reference), and adenovirus vectors (U.S. Pat. No. 5,585,362, herein incorporated by reference). Such vectors can utilize tissue-specific promoters in targeting expression to tumor cells of particular tissue types. For example, the alpha-1-antitrypsin promoter and the albumin promoter are promoters activated primarily in liver tissue; and thus, may be used to target expression of the desired polynucleotide in tumor cells of hepatic origin. Similarly, the α-fetoprotein promoter may be used to target expression of the desired polynucleotide in hepatomas. The DF3/MUC-1 promoter may be used to target expression of the desired polynucleotide in breast cancer cells.

Therapeutically effective amounts of sense polynucleotides have been administered as naked DNA or as part of a vector in successfully effecting expression of a gene in vivo with the intended therapeutic result. Several clinical trials are ongoing in which sense polynucleotides are being applied for therapeutic purposes for a wide spectrum of human diseases. Successful therapy in humans includes treating individuals having adenosine deaminase deficiency, and individuals with with ischemia. Likewise, antisense has been successfully employed to decrease gene expression (e.g., by sequence-specific base pairing with mRNA in preventing translation, or by sequence-specific base pairing with DNA in preventing transcription) in vivo for the intended therapeutic purposes. Several clinical trials are ongoing in which antisense polynucleotides are being applied for therapeutic purposes for a wide spectrum of human diseases. Successful antisense therapy in humans includes treatment of HIV infection, cytomegalovirus retinitis, myelogenous leukemia, and genital warts. Sense and antisense therapies may be applied in a site-directed manner, rather than systemically. A drawback to systemic therapies is the lack of selectively delivering the therapy to its intended target, diseased tissue, rather than to normal tissue. In that regard, activation-induced cell death of tumors has been complicated by the apparent resistance of Fas+ tumor cells to Fas-mediated cytotoxicity (see, e.g., O'Connell et al., 1996, supra). Additionally, current theory is that FasL expression by tumor cells enhances tumorigenesis (immune privilege or tumor evasion) by killing Fas expressing immune effector cells and surrounding Fas expressing tissue cells (Strand et al., 1996, supra; Shiraki et al., 1997, supra; O'Connell et al., 1996, supra Niehans et al., 1997, supra; Hahne et al., 1996, supra).

One aspect of the present invention relates to the discoveries that Fas expressed by nonadherent tumor cells (including circulating tumor cells and metastatic cells) can, unexpectedly, transduce an apoptotic signal when cross-linked by FasL; that nonadherent tumor cells develop fratricidal Fas/FasL mediated apoptosis; that the metastatic capacity of a malignant tumor can be abrogated if Fas and FasL are coexpressed in tumor cells that are nonadherent; and that FasL expression in nonadherent tumor cells may contact B cells involved in a pro-tumor immune response, and may induce Fas–mediated cytotoxicity of such B cells, thereby inhibiting or impairing the B cell involvement in progression of solid, nonlymphoid tumor and metastasis. Another aspect of the present invention relates to the discovery that administering antisense to FasL into a tumor and/or into tissue surrounding (local or regional to) the tumor (collectively or individually referred to for purposes of brevity as into the "tumor environment") resulted in a decrease in FasL expression and also resulted in reduced tumor growth.

In one embodiment of the present invention, provided is a composition comprising one or more polynucleotides, wherein the composition comprises a polynucleotide comprising sense FasL, or a polynucleotide comprising antisense FasL, or a combination thereof. In another embodiment of the present invention, provided is the use of one or more polynucleotides comprising sense FasL, or antisense FasL, or a combination thereof, in the manufacture of a pharmaceutical composition for use in a method of inhibiting tumor progression (one or more of tumor growth or metastasis) in an individual; wherein the method comprises administering a therapeutically effective amount of the composition to an individual (e.g., an individual having solid, nonlymphoid tumor or suspected of having solid, nonlymphoid tumor).

In one embodiment of the present invention, the method comprises inducing FasL expression in FasL(−) Fas+ solid, nonlymphoid tumor cells in an individual by administering to that individual a therapeutically effective amount of a composition comprising a polynucleotide encoding FasL. The polynucleotide may further comprise a vector which serves as a vehicle for introducing into, and expressing in, the targeted tumor cells a gene encoding FasL. The polynucleotide, upon entry into such tumor cells, upregulates or induces the cell-surface expression of FasL, thereby making the treated tumor cells FasL+. Thus, those Fas+ and FasL+ tumor cells in non-anchorage conditions in the treated site, or that metastasize from the treated site, may participate in the fratricidal Fas/FasL mediated apoptosis, and may also contact and induce Fas−mediated cytotoxicity of Fas+ B cells involved in a pro-tumor immune response.

In another illustration of this embodiment, the composition further comprises a affinity ligand (e.g., antibody, antigen-binding fragment thereof (Fab, Fv, $Fab_2$ or the like), lectin, aptamer, and the like) linked to the vector using conjugation methods known in the art (e.g., heterobifunctional linker, or photo-activated linker), in forming a FasL-inducing conjugate. The affinity ligand of the FasL inducing conjugate has binding specificity for a tumor-associated molecule preferentially expressed by a tumor cell, particularly by a nonadherent tumor cell. Thus, the affinity ligand facilitates selectively delivery of the vector to its intended target: Fas+ solid, nonlymphoid tumor cells, including nonadherent tumor cells (e.g., circulating tumor cells and metastatic tumor cells). In this embodiment, the composition may further comprise a pharmaceutically acceptable carrier. Such pharmaceutically acceptable carriers are known in the art to include, but are not limited to, physiological solutions (e.g., water, salt-containing solution, buffered solution), liposomes, other delivery vehicles, and compositions which facilitate infection or transfection of the tumor cell by the vector (e.g., microparticles which permit or enhance uptake or introduction of vector into the target cells).

For purposes of the description, the methods of the present invention will be illustrated in the following examples. In the following examples used to illustrate the invention, it is important to note that mice have been validated as a model for the evaluation of antitumor agents (including sense or antisense therapeutics) by those skilled in the art. Mouse models of human cancer have been shown to reflect the clinical effectiveness of antitumor agents in original patients treated with these agents; and reflects antitumor effects from the agents, such as tumor regression or inhibition of tumor growth, as consistent with the activity against the corresponding types of clinical cancer.

EXAMPLE 1

This Example illustrates the difference in the ability of tumor-expressed Fas to transmit an apoptotic signal, depending on cell adhesion status. The B16F10 melanoma cell line, well-characterized and of high metastatic potential, was selected as the FasL(−), Fas+ tumor cells in this illustration. Lack of FasL expression by B16F10 melanoma cells was confirmed by Western blot, Northern blot, and RT-PCR analyses. Fas expression by B16F10 melanoma cells was detected by flow cytometry, and RT-PCR analyses.

The ability of Fas, expressed by these melanoma cells, to transmit an apoptotic signal was tested by cross-linking of Fas with agonistic anti-Fas antibody (IgG antibody- clone Jo2, commercially available from Pharmingen). B16F10 cells were cultured in a confluent monolayer on 24 well plates, and then incubated for 48 hours with increasing concentrations of the anti-Fas antibody Jo2. The concentration of antibody added was either 0 ng/ml, 100 ng/ml, 1000 ng/ml, or 10,000 ng/ml. After antibody treatment, 1 μg/ml of ethidium bromide was added to the tissue culture medium, and the number of apoptotic cells (comprising red fluorescent cells with pyknotic nucleus) were counted using flow cytometry. An apoptosis index was calculated by dividing the number of apoptotic cells by the number of living cells. Fas cross-linkage with an agonistic anti-Fas antibody at all concentrations tested did not induce evident apoptosis of the tumor cells. Further, Fas cross-linkage with an agonistic anti-Fas antibody did not inhibit growth of B16F10 melanoma cells in an in vitro culture. These results suggest that the Fas expressed by tumor cells cultured in anchorage conditions does not efficiently transmit an apoptotic signal.

Fas+ B16F10 cells were also tested for their ability to transmit an apoptotic signal by culturing the cells in suspension (non-anchorage conditions) and then cross-linking Fas with agonistic anti-Fas antibody. The melanoma cells ($10^4$ cells per well in a 24 well plate) were cultured in a suspension in a fibrin clot (1.5 ml), and then incubated for 48 hours with increasing concentrations of the anti-Fas antibody Jo2 (at 0 ng/ml, 100 ng/ml, 1000 ng/ml, or 10,000 ng/ml). After antibody treatment, the number of cell colonies per well were counted under phase contrast microscopy for determining incidence of apoptosis. The number of colonies were compared to the number of colonies in the control (no antibody added) in determining the % colony inhibition. The percentage of colony inhibition was calculated using the formula:

$$100 \times [N_c - N_e]/N_c$$

wherein Nc is the number of colonies in the control, and Ne is the number of colonies in each concentration of antibody (>0 ng/ml). Fas cross-linkage with an agonistic anti-Fas antibody induced dose-related reductions in the number of B16F10 cell colonies, and a corresponding increase in the % colony inhibition. That colony formation in non-anchorage conditions was significantly reduced in the presence of agonistic anti-Fas antibody indicates that tumor-expressed Fas can transmit apoptotic signals in tumor cells grown in non-anchorage conditions.

EXAMPLE 2

This Example illustrates the differences in tumor growth and metastatic behavior in Fas/FasL normal mammals of tumor cells either FasL+ or FasL(−). In this illustration, B16F10 melanoma cells were transfected with a mammalian expression vector containing FasL cDNA. The nucleotide sequence of the human FasL gene is provided herein as SEQ ID NO: 1 (as described previously, e.g., Takahashi et al., 1994, *Int. Immunol.* 6:1567–74) and may be used as a polynucleotide for administering to a human in a method according to the present invention. Other mammalian FasL nucleotide sequences are also known to those skilled in the art (Peitsch and Tschopp, 1995, *Mol. Immunol.* 32:761–72; Suda et al., 1993, *Cell* 75:1169–78; SEQ ID NO:2) or may be derived from an amino acid sequence comprising FasL (e.g., SEQ ID NO:3). For purposes of illustration, and not limitation, a polynucleotide comprising FasL (SEQ ID NO:2) was subcloned into pCDNA3 (commercially available from Invitrogen) downstream and operably linked to the cytomegalovirus (CMV) promoter using a restriction enzyme (XbaI). Restriction enzyme digestion of plasmid DNA from individual clones with PstI distinguished clones in the positive orientation (the FasL gene operatively linked to the promoter for expression) versus clones in the reverse orientation. B16F10 cells were transfected with plasmid DNA containing the FasL gene in a positive orientation, using a transfection reagent (lipofectin). Selection for transfected cells was performed by the addition of G418 (neomycin) to the culture. Following cell selection, the transfected cells were cloned by limiting dilution in the presence of neomycin. Expression of FasL by the transfected B16F10 clones was then confirmed by RT-PCR (mRNA level) and by flow cytometry (protein level). As a control, the same process of transfection and cloning was performed using pCDNA3 alone (e.g., without the FasL cDNA insert).

FasL mRNA was detected from the transfected B16F10 cells by isolating RNA from the cells by lysis in guanidine thiocyanate followed by phenol chloroform extraction and ethanol precipitation. cDNA was synthesized using AMV reverse transcriptase and primers according to the manufacturers directions. FasL cDNA was amplified by using polymerase chain reaction and SEQ ID NO:4 as the sense primer and SEQ ID NO:5 as the antisense primer. The reactions were carried out in a 50 $\mu$l volume with 0.1 $\mu$M of each primer, 50 $\mu$M dNTP, and 1.5 mM $MgCl_2$. Denaturing was done at 96° C. for 15 seconds, annealing at 55° C. for 30 seconds and polymerization for 72° C. for 3 minutes, for 40 cycles. The result of the polymerase chain reaction using these two primers was an amplified product of 538 base pairs (bp). The 538 bp amplified product was purified by agarose gel electrophoresis and visualized with ethidium bromide staining. As controls, the RT-PCR technique was performed using RNA from B16F10 cells, and from B16F10 cells transfected with pCDNA3 only. The agarose gel electrophoresis showed that B16F10 (untransfected) cells, and B16F10 cells transfected with pCDNA3, lack detectable FasL mRNA expression (absence of any bands); whereas B16F10 cells transfected with the polynucleotide comprising pCDNA3 containing the FasL cDNA insert show significant FasL mRNA expression (presence of a 538 bp band).

FasL expression was detected on transfected B16F10 cells by harvesting the cells in culture by gentle scraping. Cells were washed in phosphate buffered saline (PBS), fixed with 3% paraformaldehyde, and then incubated with biotinylated anti-FasL (Jo2) for 30 minutes at 4° C., and washed in PBS (containing 2% FCS). Conjugate (phycoerythrin-conjugated streptavidin) was incubated with the cells for 30 minutes at 4° C. Cells were washed again in PBS, and flow cytometric analysis was performed at 610 nm. Cells in each sample were simultaneously measured for forward light scatter, side scatter, and green fluorescence and red fluorescence emissions. The data was stored and analyzed using standard methods of analysis. Quantitation of FasL expression was based on an examination of 10,000 cells for each determination as measured by semiautomatic evaluation. Flow cytometric analysis showed that B16F10 cells transfected with pCDNA3 only lack detectable FasL expression, whereas B16F10 cells transfected with pCDNA3 containing the FasL cDNA insert show FasL expression.

To determine whether Fas/FasL coexpression in tumor cells could influence growth of the tumors in vitro, compared was the ability to grow these cells in adherent (monolayer) conditions. One thousand transfected B16F10 cells (pCDNA3 with FasL cDNA insert; Fas+/FasL+) were cultured in 1.5 ml of tissue culture medium supplemented with 10% FBS per well in 24 well plates. As controls, either one thousand B16F10 cells (untransfected) or one thousand B16F10 cells transfected with pCDNA3 only (Fas+/FasL(−)) were cultured in 1.5 ml of tissue culture medium supplemented with 10% fetal bovine serum (FBS) per well in 24 well plates. In comparing the growth in monolayers, clones of the Fas+/FasL+ B16F10 cells were able to grow in monolayer with the same efficiency in culture as the Fas+/FasL(−) control B16F10 cells (untransfected or transfected with pCDNA3 only).

To determine whether Fas/FasL coexpression in tumor cells could influence growth of the tumors in vitro, compared was the ability to grow these cells in nonadherent (non-anchorage) conditions. One thousand transfected B16F10 cells (pCDNA3 with FasL cDNA insert; Fas+/FasL+) were cultured in 1.5% agarose per well in 24 well plates. As controls, either one thousand B16F10 cells (untransfected) or one thousand B16F10 cells transfected with pCDNA3 only (Fas+/FasL(−)) were cultured in 1.5% agarose per well in 24 well plates. B16F10 cells (untransfected), and B16F10 cells transfected with pCDNA3 only showed the same efficiency in forming colonies in non-anchorage conditions; e.g., after 5 days, cells develop an average of about 150 colonies. Each colony is a compact cluster of several hundreds of cells. However, three separate clones of B16F10 cells transfected with pCDNA3 with FasL cDNA insert failed to develop a significant number of colonies. When a colony did develop from these transfected cells, the colony comprised a small cell cluster of about 5 to about 20 loosely associated cells. A conclusion from these results is that in nonadherent (e.g., non-anchorage) conditions, Fas/FasL coexpressing tumor cells develop fratricidal Fas/FasL mediated apoptosis. Thus, one in vivo mechanism of inhibiting tumor progression by administering a therapeutically effective amount of a composition comprising a polynucleotide encoding FasL ("FasL sense polynucleotide") comprises inducing activation-induced cell death in nonadherent FasL(−) Fas+ tumors. The Fas+/ FasL+ tumor cells may then be susceptible to Fas-dependent apoptosis by interaction with Fas+/FasL+ cells from the same tumor ("fratricidal Fas/FasL mediated apoptosis").

To further evaluate the effect that FasL expression has on non-adherent tumor cells in vivo, a model for metastatic growth was used. Direct intrasplenic implantation of melanoma cells (e.g. B16F10) yield large splenic tumors. For example, injection of $10^5$ B16F10 melanoma cells intrasplenically yields large splenic tumors in 14 days. For 5 days after the injection, the B16F10 cells grow in the spleen forming clusters without visible intercellular connective matrix, thereby mimicking metastatic growth in the lymphatic sinuses (i.e., non-anchorage conditions). After this early period, desmoplastic and angiogenic reactions complete the structure of the tumor tissue. If a mechanism of action is Fas–dependent apoptosis of Fas+ tumor cells, then in vivo, intra-splenic tumor formation should also be impaired irrespective of the influence of lymphocyte deletion. In this in vivo standard experimental model, five groups of C57BL/6 mice were injected intrasplenically with $10^4$ tumor cells; and a sixth group did not receive tumor cells (control). One group received B16F10 cells; a second group received B16F10 cells transfected with pCDNA3 only (Fas+, FasL(−)); and groups three, four, and five received B16F10 cells transfected with a FasL sense polynucleotide comprising pCDNA3 containing FasL cDNA (Fas+, FasL+; either one of clones 3, 4, and 7). Fourteen days postinjection, spleens from the three groups of mice were evaluated for tumor growth by measuring spleen weight, by visual observation, and by histological evaluation. For spleen weight determinations, the spleens were removed; dried by immersion in 100% ethanol for seven days during which period the ethanol evaporated; and the dried spleens were weighed and an average for the group reported. As shown in FIG. 1, spleen weight was significantly increased, and macroscopic tumor growth was observed, in mice injected with B16F10 cells ("B16F10") or B16F10 cells transfected with pCDNA3 only ("Fas+/FasL− B16"), as compared to the spleen of a control group of mice receiving only a PBS injection. However, the spleens of mice receiving B16F10 cells transfected with a FasL sense polynucleotide did not show a significant increase in weight. Visually and histologically, the spleens of the Fas+/FasL+ B16 injected mice showed a normal structure with numerous isolated tumor cells with apoptotic nuclei. These analyses are indicative of a failure of tumor progression. This is an unexpected result because it has been reported that FasL+ expression by tumor cells represents a significant advantage for tumor survival and tumor growth (e.g., via immune privilege). In contrast, the results of this standard animal model indicate that FasL+ expression by tumor cells, at least in nonadherent conditions, represents a mechanism by which tumor cell growth is inhibited or impaired. These results in vivo confirm the results obtained in vitro, and further support a method for inhibiting tumor progression in individuals having FasL(−) Fas+ tumors by administering in vivo a therapeutically effective amount of a composition comprising a FasL sense polynucleotide. As demonstrated herein, the method is facilitated, at least in part, by Fas-mediated cytotoxicity of the tumor (fratricidal Fas/FasL mediated apoptosis).

EXAMPLE 3

Figure 2:
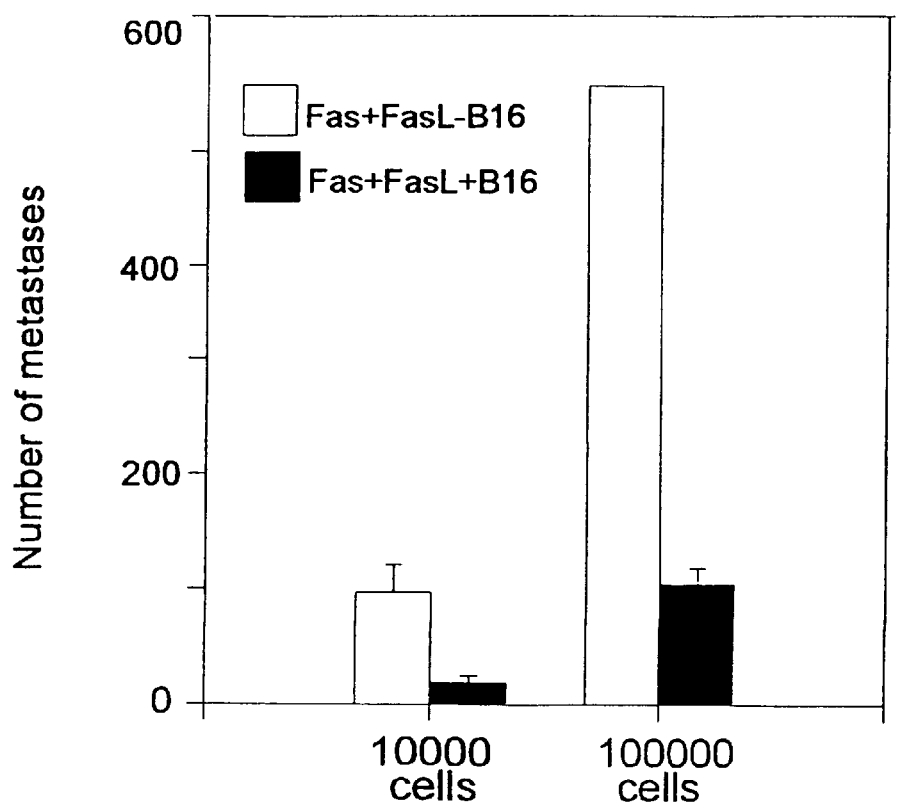
FIG. 2 is a bar graph illustrating the number of lung metastases in mice receiving Fas+, FasL+ B16 cells as compared to the number of lung metastases in mice receiving Fas+, FasL− cells.

This Example further illustrates the differences in tumor growth and metastatic behavior in Fas/FasL normal mammals of Fas+ tumor cells that are either FasL+ or FasL(−). Methods and compositions for producing Fas+FasL− B16 transfected cells (containing pCDNA3) and Fas+FasL+ B16 transfected cells (containing pCDNA3 with FasL cDNA insert) have been described herein in Example 2. It is known by those skilled in the art that B16F10 melanoma cells have a characteristic ability, common among melanomas, to develop lung metastases. Lung metastases formation involves cell arrest (non-anchorage conditions), extravasation (anchorage condition), and colony formation (anchorage/non-anchorage conditions). To evaluate the effect of FasL expression by tumors on lung metastasis, this experimental animal model for in vivo metastatic growth was used. One group of C57BL/6 mice was injected via the tail vein with $10^5$ B16F10 cells transfected with pCDNA3 only ("Fas+/FasL− B16"). A second group of C57BL/6 mice was injected via the tail vein with $10^5$ B16F10 cells transfected with a FasL sense polynucleotide comprising pCDNA3 containing FasL cDNA ("Fas+/FasL+ B16"). Lungs from the two groups of mice were evaluated for tumor growth by visual observation. Fourteen days postinjection, the lungs from mice receiving B16F10 cells developed numerous macroscopic lung metastases, whereas macroscopic lung metastases were few or absent in mice receiving Fas+/FasL+ B16 cells. The experiment was repeated using an inoculum of either $10^4$ or $10^5$ B6F10 or Fas+, FasL+ B16 clones. Three weeks postinjection, the lungs were removed, fixed in ethanol, and sliced (approximately 0.5 mm thick) for histological examination. The number of metastases per mouse was counted on lung slices using a 10× microscope, and the average count of metastases per mouse for each test group was calculated. As shown in FIG. 2, there is a significant reduction in the number of lung metastases in mice receiving Fas+, FasL+ B16 cells as compared to the number of lung metastases in mice receiving B6F10 cells (Fas+, FasL−). Using the same experimental animal model for in vivo metastatic growth, two groups of mice were monitored for an extended period of time. One group was injected via the tail vein with B16F10 cells, whereas the other group was injected with Fas+, FasL+ B16 cells. After 30 days postinjection, all mice in the group injected with B16F10 cells died. Postmortem analysis of the lungs disclosed sufficient metastatic growth consistent with being the cause of death of this group of mice. However, all mice in the group injected with Fas+, FasL+ B16 cells survived the 30 day period.

It can be concluded from this experimental animal model of metastatic growth in vivo that FasL+ expression by Fas+ tumor cells, at least in nonadherent conditions, represents a mechanism by which metastases are inhibited or impaired, rather than being a significant advantage for tumor survival and tumor growth. These results confirm the results demonstrated in Example 2 herein, and further support a method for inhibiting tumor progression in individuals having FasL(−) Fas+ tumors by administering in vivo a therapeutically effective amount of a composition comprising a FasL sense polynucleotide.

EXAMPLE 4

This Example further illustrates that the metastasis inhibitory effect of FasL expressing Fas+ tumor cells in non-anchorage conditions is, at least in substantial part, Fas/FasL mediated. That is, that fratricidal apoptosis comprises a substantial portion of such observed metastasis inhibitory effect, and that Fas+ coexpression is necessary for the fratricidal activity. In this illustration, used were the in vitro culture methods, experimental animal model, and compositions described in Examples 2 and 3 herein. However, in this example, the tumor cells used were Lewis lung carcinoma cells (3LL). The 3LL cells used were shown to be Fas− by both flow cytometry and by RT-PCR. Further, agonist anti-Fas antibody, Jo2, did not induce apoptosis of these cells when the cells were cultured in monolayers (anchorage conditions) nor inhibit colony formation when cultured in fibrin clots (non-anchorage conditions). The 3LL cells were transfected with a FasL sense polynucleotide (e.g., pCDNA3 containing a FasL cDNA insert operaively linked thereto for expression of FasL). 3LL clones expressing FasL were identified by RT-PCR. When Fas−/FasL+ 3LL clones were cultured in vitro in non-anchorage conditions, they were able to produce colonies comparable to those produced by 3LL cells and by 3LL cells transfected with pCDNA3 only (Fas−/FasL(−)). A conclusion from these results is that in the absence of Fas expression, the expression of FasL alone does not induce the fratricidal effect.

Figure 3:
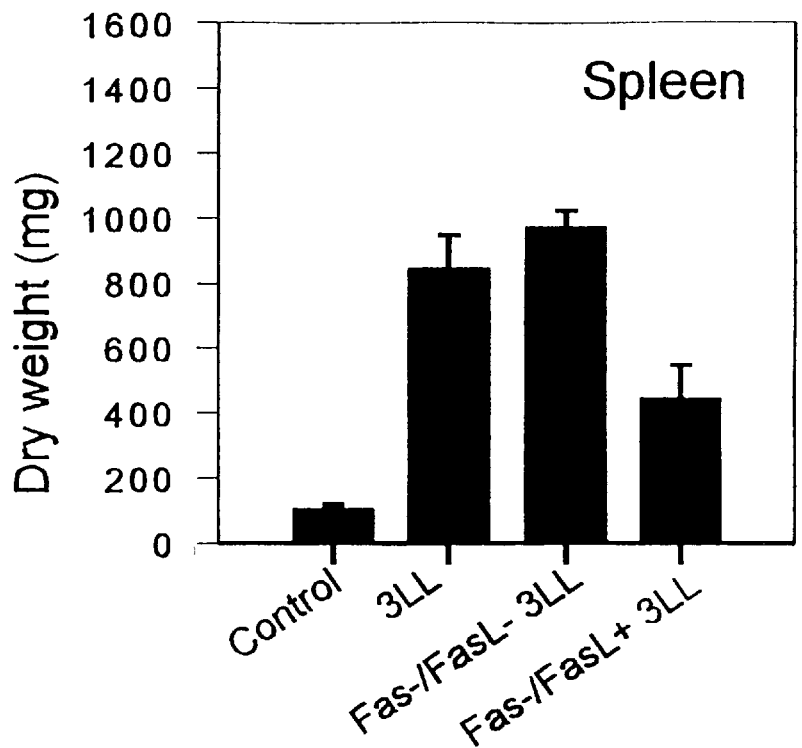
FIG. 3 is a bar graph illustrating tumor growth (as measured by spleen weight) in mice injected with 3LL cells ("3LL"); or 3LL cells transfected with pCDNA3 only ("Fas−/FasL− 3LL"); or PBS; or 3LL cells transfected with pCDNA3 containing FasL cDNA ("Fas−/FasL+ 3LL").

In the experimental animal model for metastatic growth, 3LL cells or transfected 3LL cells were directly implanted in the spleen. After fourteen days, the spleens were harvested, dried, and weighed as described above. As shown in FIG. 3, spleen weight was significantly increased, and macroscopic tumor growth, was observed in mice injected with 3LL cells ("3LL") or 3LL cells transfected with pCDNA3 only ("Fas−/FasL− 3LL"), as compared to the spleen of a control group of mice receiving only a PBS injection. Spleens of mice receiving 3LL cells transfected with pCDNA3 containing FasL cDNA ("Fas−/FasL+ 3LL") showed a significant increase in weight as compared to the controls, and macroscopic tumor growth was evident. While the Fas−/FasL+ 3LL cells produced tumor of smaller size than 3LL, Fas−/FasL+ 3LL cells produced significantly more tumor growth in the spleen than that observed for Fas+/FasL+ B16 cell implantation.

Figure 4:
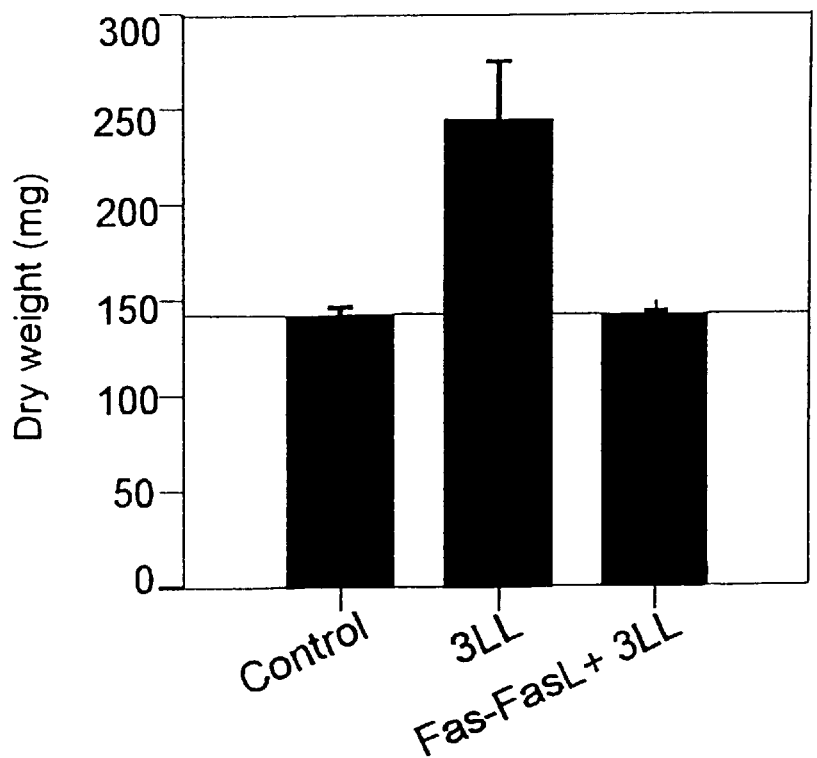
FIG. 4 is a bar graph illustrating the number of lung metastases in mice receiving 3LL cells or Fas−/FasL+ 3LL cells.

In the experimental animal model for lung metastases, 3LL cells or transfected 3LL cells were injected into mice via the tail vein. After fourteen days, the lungs were analyzed for the presence of metastases by drying, and weighing the lungs as described above for the spleen. As shown in FIG. 4, lung weight and the number of metastases was significantly increased in mice injected with 3LL cells as compared to the lungs of a control group of mice receiving only a PBS injection. Lungs of mice receiving 3LL cells transfected with pCDNA3 containing FasL cDNA ("Fas−/FasL+ 3LL") produced a significantly lower number of lung metastases as compared to mice receiving 3LL cells.

Taken together, the studies using 3LL cells and 3LL transfected cells indicate that there is another mechanism, in addition to the Fas-mediated cytotoxicity of the tumor (fratricidal Fas/FasL mediated apoptosis), involved in inhibiting tumor progression. One possibility is that expression of FasL by circulating tumor cells induces changes in the cellular microenvironment which counter the progression of metastases.

EXAMPLE 5

This Example illustrates that expression of FasL by nonadherent tumor cells can interact with Fas+ B cells to induce Fas-mediated cytotoxicity, thereby inhibiting the B cell involvement in promoting tumor progression and metastasis. Further, expression of FasL by nonadherent tumor cells also induces a change in the CD4/CD8 ratio that may play a role in the metastasis inhibitory effect of FasL expressing nonadherent tumor cells (such as in non-anchorage conditions). In this illustration, used were the experimental animal models, and compositions described in Examples 2 and 3 herein, to assess for alterations in lymphocyte populations. Three groups of C57BL/6 mice were injected subcutaneously. One group received $10^5$ B16F10 cells; and another group received $10^5$ Fas+/FasL+ B16 transfected cells. A third group received saline only, as a control. Three weeks postinjection, the spleens of each group of mice were removed, dispersed, and mononuclear cells selected by density gradient. The mononuclear cells were stained with fluorescent labeled monoclonal antibodies to detect CD3 (pan T lymphocyte), CD4 (T helper cells), CD8 (T suppressor cells), and CD19 (pan B lymphocytes) surface markers as detected and quantitated by flow cytometry. The relative frequency of each cell type is expressed as a percentage of total positively stained cells ± standard deviation. As shown in FIG. 5, the spleens of mice receiving Fas+/FasL+ B16 cells had a significant increase of the T cell to B cell ratio, and an increased CD4 to CD8 ratio, as compared to the spleens of mice receiving either B16F10 cells, or saline control. These results indicate that expression of FasL on tumor cells induces certain systemic changes in lymphocyte populations, with a relative increase in T cell numbers (primarily CD4+), and a relative reduction in B lymphocyte populations. This is an unexpected result because it has been reported that FasL+ expression by tumor cells confers immune privilege to the tumor cells by mediating apoptosis of activated T cells (see, e.g., Strand et al., 1996, supra; Niehans et al., 1997, supra; O'Connell et al., 1996, supra; and Shiraki et al., 1997, supra). In contrast, the results of this standard animal model indicate that FasL+ expression by tumor cells, at least in non-anchorage conditions, represents: a mechanism by which systemically T cells are either directly or indirectly activated to mediate inhibition or impairment of metastasis, or a mechanism by which B cells are reduced thereby mediating inhibition or impairment of metastasis, or a combination thereof.

To assess which of these altered lymphocyte populations (T or B cells) are effector cells of, at least part of, the metastasis inhibitory effect observed with FasL expressing tumor cells, specific immunodeficient mice were used. One group of athymic (T cell deficient) nude ("nu/nu") mice was injected intra-splenically with $5 \times 10^5$ Fas+/FasL+ B16 cells. One group of muMT/muMT ("B cell deficient"; i.e., do not develop competent B cell system) mice was injected intrasplenically with $5 \times 10^5$ Fas+/FasL+ B16 cells. One group of C57BL/6 (immunocompetent) mice was injected intrasplenically with $5 \times 10^5$ Fas+/FasL+ B16 cells. One group (control) received PBS only. One week postinjection, all groups were injected via the tail vein with $10^5$ B16F10 cells suspended in PBS. Two weeks after injection of B16F10 cells, lung metastases were counted under phase contrast microscopy. The metastasis inhibitory effect of the tumor cells was calculated using the formula:

[100×(number of metastases in control—number of metastases in the test)/number of metastases in the control].

As illustrated in FIG. 6, the control group, by definition, showed no metastasis inhibitory effect; and the immunocompetent mice ("C57BL/6") and B cell deficient mice ("muMT/muMT C57BL/6") showed very high inhibitory effects on development of metastases related to the subsequent B16F10 cell injections. In contrast, T cell deficient, B cell competent mice did not show significant metastasis inhibitory effects. These results show that in this model, Fas+/FasL+ B16 cells produce statistically and significantly less metastases in muMT/ muMT (B cell deficient) mice than in C57BL/6 (B cell competent) mice. This is evidence that (a) B cells can promote tumor progression and metastasis, and (b) a reduction of B cells, such as by Fas-mediated cytotoxicity induced by contact with FasL(+) tumors, is a mechanism for increasing the metastasis inhibitory effect (i.e., for inhibiting tumor progression). It is noted that such interactions between Fas+ B cells and FasL(+) tumor may primarily take place in tumor tissue (infiltrating B cells), and in lymphoid tissues either regional or distal to the site of primary tumor. Such B cells, or a subpopulation thereof, may promote tumor progression.

EXAMPLE 6

This Example illustrates that the metastasis inhibitory effect (e.g., inhibition of tumor progression) observed of FasL expressing circulating tumor cells is systemic, rather than local. In this illustration, used were the experimental animal models, and compositions described in Examples 2 and 3 herein. Five groups of C57BL/6 were injected intrasplenically. One group received normal saline (control); one group received $10^5$ B16F10 cells; one group received $10^5$ irradiated B16F10 cells; one group received $10^5$ Fas+/FasL+ B16 cells; and one group received $10^5$ irradiated Fas+/FasL+ B16 cells. Seven days postinjection, all groups were injected, via the tail vein, with $10^5$ B16F10 cells. Two weeks after the challenge with $10^5$ B16F10 cells, the spleens and lungs of the mice were analyzed for tumor burden by weight, and macroscopically. The control group had developed extensive lung metastases, while lacking development of splenic tumor. In contrast, the group of mice receiving the splenic injection of B16F10 cells had well developed splenic tumor (averaging between 1500 to 2000 mg/ spleen), but less extensive lung metastases when compared to the control group. These results suggest that the well-developed splenic tumor (Fas+/FasL(−)) inhibited the growth of lung metastases through a systemic mechanism.

Further, the group of mice receiving irradiated B16F10 cells had levels of splenic tumor (very low) and lung metastases (extensive) comparable to the control group. The group of mice injected with Fas+/FasL+ B16 cells did not develop splenic tumors; however, the number of lung metastases was significantly reduced when compared to the controls. When comparing the number of lung metastases, mice injected with Fas+/FasL+ B16 cells (not developing splenic tumors) and mice injected with B16F10 cells (Fas+/FasL(−); having well developed splenic tumor) were similar in efficacy in inhibiting the growth of lung metastases through a systemic mechanism. Thus, while Fas+/FasL+ B16 cells tumor cells did not develop splenic tumors, these tumor cells had similar efficacy in exerting or inducing a distant inhibitory effect, as compared to well developed splenic tumor (Fas+, FasL(−) cells), on lung metastases.

It is important to note that (a) Fas+, FasL+ B16 cells injected intrasplenically are effective in significantly reducing the number of lung metastases formed from Fas+, FasL+ B16 cells; and that (b) Fas+, FasL+ B16 cells injected intrasplenically are effective in significantly reducing the number of lung metastases formed from Fas+, FasL(−) B16F10 cells. These results indicate that through a process reaching systemically, FasL+ Fas+ tumors can directly and/or indirectly mediate a metastasis inhibitory effect (e.g., such as by fratricidal apoptosis) of either FasL+ or FasL(−) tumor cells that express Fas, and/or of Fas expressing B cells involved in a pro-tumor immune response (e.g., such as by Fas mediated cytotoxicity). As can be further concluded from these results, this FasL+ mediated metastasis inhibitory effect requires tumor cell proliferation/turnover, as irradiated Fas+, FasL+ B16 cells appeared ineffective in inhibiting metastasis.

EXAMPLE 7

This Example illustrates one embodiment of a method according to the present invention for inhibiting tumor growth and metastasis. Provided is a method for causing FasL expression in FasL(−) Fas+ tumor cells, wherein the FasL(−) Fas+ tumor cells become FasL+ and can be used to contact and induce Fas mediated cytotoxicity of Fas expressing cells selected from the group consisting of tumor cells, B cells (primarily, but not limited to, those involved in a pro-tumor immune response), and a combination thereof. The method comprises contacting the tumor cells with a therapeutically effective amount of a compositionn comprising a FasL sense polynucleotide. The polynucleotide may further comprise an expression vector; wherein the vector is a vehicle for introducing into, and expressing in, the tumor cells, particularly nonadherent tumor cells, a polynucleotide encoding FasL. Methods for making such a vector are previously described herein in more detail. The polynucleotide, upon entry into such tumor cells, upregulates or induces the cell-surface expression of FasL, thereby making the treated Fas+ tumor cells FasL+. In another illustration of this embodiment, the polynucleotide further comprises an affinity ligand linked to the expression vector, in forming a FasL-inducing conjugate. The affinity ligand of the FasL inducing conjugate has binding specificity for a tumor-associated molecule preferentially expressed by a tumor cell, and particularly by a nonadherent tumor cell. Thus, the affinity ligand facilitates selectively delivery of the expression vector to its intended target tumor cells. In this embodiment, the polynucleotide further comprises a pharmaceutically acceptable carrier. Such pharmaceutically acceptable carriers are known in the art to include, but are not limited to, physiological solutions, liposomes, other delivery vehicles, and compositions which facilitate infection or transfection of the tumor cell by the polynucleotide (e.g., microparticles which permit or enhance uptake or introduction of vector into the target cells).

Using methods known in the art of molecular biology, including methods described above, various promoters and enhancers (see, e.g., SEQ ID NO:6) may be operably linked to the polynucleotide encoding FasL to increase the expression of FasL. The selection of the promoter will depend on the such factors as the composition of the polynucleotide (e.g., sequence composition, if a vector used), and if tissue specific expression is desired. The promoter is operably linked to the polynucleotide encoding FasL, and may be part of the vector sequence or introduced as part of the DNA insert containing the FasL encoding sequence. The vector may include other control elements for efficient gene transcription or message translation, including enhancers, and regulatory signals. Accordingly, a polynucleotide encoding FasL be ligated into an expression vector at a specific site in relation to the vector's promoter, control, and regulatory elements so that when the recombinant vector is introduced into the target tumor cell, the FasL DNA sequences can be expressed.

There are several means by which to administer to an individual the composition comprising one or more polynucleotides according to the present invention. In the situation in which a primary solid, nonlymphoid Fas+ tumor in a specific organ is detected, a catheter may be inserted into one or more of the major vessels (blood or lymphatic) that enter or exit from that organ using standard methods for inserting the catheter into such vessels, as known to those skilled in the art. This "site-directed" treatment may comprise either a single infusion, or multiple infusions over time, of a therapeutically effective amount of the composition, as monitored by treatment response and by indicia of any possible local toxicity in the treated organ.

In another embodiment, the composition may be administered systemically by intravenous injection. The intravenous injection procedure may also be facilitated by the use of a catheter. The embodiment of intravenous injection may be particularly preferred for circulating tumors present throughout the bloodstream. The composition may be introduced directly ("direct transfer") resulting in expression of the genetic material into the target tumor cells has been demonstrated by techniques in the art such as by injecting intravenously an expression plasmid:cationic liposome complex (Zhu et al., 1993, *Science* 261:209–211), or as naked DNA. It is appreciated by those skilled in the art that a composition comprising a vector comprising the polynucleotide may be linked to a affinity ligand, and the resultant conjugate may bind to the nonadherent tumor cells, and may be endocytosed by the tumor cell. Other methods of promoting the introduction of therapeutic molecules, such as vectors or vectors linked to affinity ligands (conjugate, into cells in the bloodstream are known in the art. In that regard, methods and devices for ex vivo or in vivo electroporating therapeutic molecules into cells in the blood have been described previously (see, e.g., U.S. Pat. Nos. 5,507,724 and 5,545,130).

In another example, Fas+ tumor cells, removed from an individual, can be transfected or electroporated by standard procedures known in the art, resulting in the introduction of the polynucleotide encoding FasL into the cells. The FasL+ tumor cells may then be selected for using methods known in the art (e.g., a selection marker of the expression vector), and the selected cells may then be used as a vehicle for introduction of the polynucleotide into a heterologous individual. In a preferred embodiment, the composition may be administered to the individual by intra-tumoral injection.

EXAMPLE 8

This Example illustrates a polynucleotide comprising FasL antisense, and the ability of FasL antisense to reduce tumor growth. A nucleotide sequence of which antisense FasL may be comprised or derived therefrom is provided herein as SEQ ID NO:7 and may be used for administering to a human in a method according to the present invention. Other mammalian antisense FasL nucleotide sequences may be derived from the various FasL sequences known to those skilled in the art (see, e.g., SEQ ID NO:8). As an illustrative non-limiting example, an antisense FasL polynucleotide was produced by cloning antisense FasL (SEQ ID NO:8) into pCDNA3 downstream and operably linked to the cytomegalovirus (CMV) promoter using a restriction enzyme (XbaI). Restriction enzyme digestion of plasmid DNA from individual clones with PstI distinguished clones in the antisense orientation from those in a positive orientation. The antisense FasL polynucleotide was then used to transfect tumor cells in vivo. In this experiment, human colorectal carcinoma cell line SW620 ($10^5$ cells) was injected subcutaneously into each of a group of nu/nu mice. When the tumor reached 5 mm in diameter, the anti-sense FasL polynucleotide was injected intratumorally at 5 day increments for a total of 3 injections (50 μg of vector in 100 μg of saline). Twenty five days after the first injection, tumor was harvested and analyzed for the presence of the antisense FasL polynucleotide by polymerase chain reaction and agarose gel electrophoresis. The results of the analysis show that the antisense FasL polynucleotide remains available for translation in the tumor for at least 25 days after injection. Using an enzyme-linked immunoassay, the sera from the group of treated mice was analyzed for soluble FasL. The analysis showed that mammals which received a therapeutically effective amount of the antisense FasL polynucleotide demonstrated a significant (group average of about 40%) decrease in the serum concentration of soluble FasL as compared to control mice not receiving antisense FasL. It may be concluded from these results that FasL antisense polynucleotide, when administered in a therapeutically effective amount to an individual, can result in a biological effect in vivo.

Figure 7:
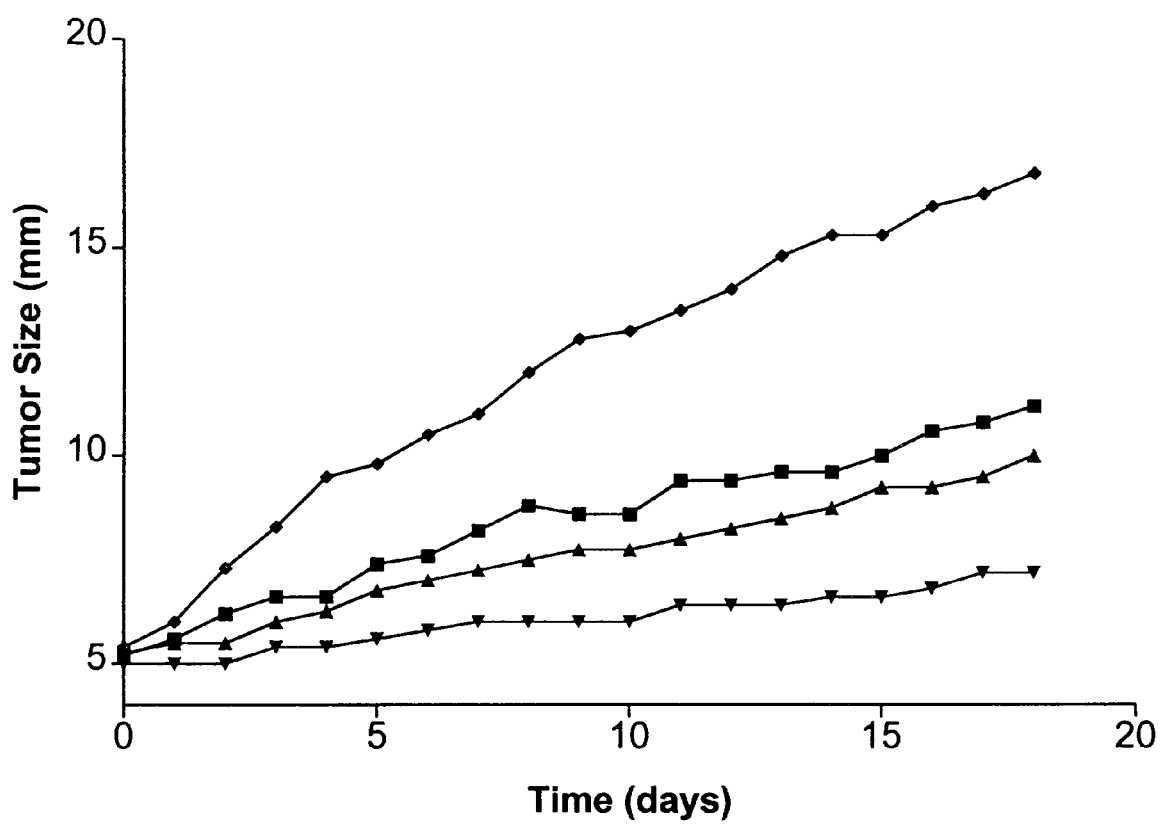
FIG. 7 is a graph illustrating the effect of one or more polynucleotides on the rate of tumor growth (tumor size plotted against time).

To determine whether administering a therapeutically effective amount of a composition according to the present invention into the tumor environment of an individual can inhibit tumor growth, nu/nu mice were injected subcutaneously with $10^5$ SW620 tumor cells. When the tumors reached 5 mm in diameter, the mice were divided into four groups. A first group ("control") received intra-tumoral injections at 5 day increments for a total of 3 injections of plasmid DNA without any inserted antisense polynucleotide (50 μg of vector in 100 μg of saline). A second group received intra-tumoral injections at 5 day increments for a total of 3 injections of a polynucleotide comprising an expression vector with antisense FasL operatively inserted therein for expression (50 μg of antisense FasL vector in 100 μg of saline). A third group received intra-tumoral injections at 5 day increments for a total of 3 injections of a polynucleotide comprising an expression vector with sense FasL operatively inserted therein for expression (50 μg of sense FasL vector in 100 μg of saline). A fourth group received intra-tumoral injections at 5 day increments for a total of 3 injections of a combination of polynucleotides comprising (a) the antisense FasL polynucleotide (50 μg of antisense FasL vector in 100 μg of saline), and the sense FasL polynucleotide (50 μg of sense FasL vector in 100 μg of saline). Tumor growth was then monitored daily, and the daily rate of tumor growth was determined by the number of days it took for the average tumor diameter of each group to reach 15 mm. As shown in FIG. 7, it took approximately 18 days for the control group (-♦-) to reach an average tumor diameter of 15 mm. In comparison to the control group, the groups receiving a therapeutically effective amount of either a polynucleotide comprising sense FasL (-■-), a polynucleotide comprising antisense FasL (-▲-) or a polynucleotide combination comprising sense FasL and antisense FasL (-▼-) showed a statistically significant inhibition in the rate of tumor growth. In this experiment, the polynucleotide combination showed the strongest inhibitory effect on tumor progression.

It may be concluded from these results that a composition comprising one or more polynucleotides according to the present invention, when administered in a therapeutically effective amount to effect inhibition of tumor progression, can be introduced into the tumor environment of an individual in a method of inhibiting tumor progression according to the present invention.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A method for inhibiting tumor progression in an individual, the method comprising administering intratumorally into a solid tumor of the individual a composition comprising one or more polynucleotides selected from the group consisting of FasL antisense polynucleotide for inhibiting expression of the FasL gene, and a combination of a FasL sense polynucleotide and FasL antisense polynucleotide, wherein the FasL polynucleotide and FasL antisense polynucleotide do not comprise complementary strands on the same double stranded polynucleotide; wherein the one or more polynucleotides are operably linked to one or more control elements that enable expression thereof in the solid tumor of the individual into which the one or more polynucleotides enter; wherein the tumor comprises tumor cells selected from the group consisting of Fas+/FasL− tumor cells, Fas−/FasL− tumor cells, and Fas−/FasL+ tumor cells; and wherein the composition is administered in a therapeutically effective amount to inhibit tumor progression.

2. The method according to claim 1, wherein the composition further comprises a pharmaceutically acceptable carrier selected from the group consisting of a physiological solution, liposomes, and a delivery vehicle, which facilitates entry of the composition into the cells.

3. The method according to claim 1, wherein the composition is administered to the solid tumor by using a catheter.

4. The method according to claim 1, wherein the composition comprises one or more polynucleotides consisting of the combination of a FasL sense polynucleotide and FasL antisense polynucleotide, and further comprises an expression vector containing the FasL sense polynucleotide operatively linked to a promoter for expression.

5. The method according to claim 1, wherein the composition comprises FasL antisense polynucleotide, and further comprises an expression vector containing the FasL antisense polynucleotide operatively linked to a promoter for expression.

6. The method according to claim 1, wherein the composition comprises the combination of a FasL sense polynucleotide and antisense FasL polynucleotide, and further comprises an expression vector containing the FasL sense polynucleotide operatively linked to a promoter for expression, and an expression vector containing the FasL antisense polynucleotide operatively linked to a promoter for expression.

7. A composition comprising a combination of polynucleotides comprising a FasL sense polynucleotide, and a FasL antisense polynucleotide for inhibiting expression of the FasL gene; wherein each polynucleotide is operably linked to one or more control elements that enable expression in mammalian cells into which the polynucleotide enters; and wherein the FasL polynucleotide and FasL antisense polynucleotide do not comprise complementary strands on the same double stranded polynucleotide.

8. The composition according to claim 7, wherein the composition further comprises a pharmaceutically acceptable carrier selected from the group consisting of a physiological solution, liposomes, and a delivery vehicle, which facilitates entry of the composition into the cells.

9. The composition according to claim 8, wherein the FasL sense polynucleotide further comprises an expression vector containing the FasL sense polynucleotide operatively linked to a promoter for expression, and the FasL antisense polynucleotide further comprises an expression vector containing the FasL antisense operatively linked to a promoter for expression.

10. A method for producing a pharmaceutical composition for inhibiting tumor progression in an individual, wherein the method comprises combining FasL sense polynucleotide with a FasL antisense polynucleotide and with a pharmaceutically acceptable carrier; wherein the FasL polynucleotide and FasL antisense do not comprise complementary strands on the same double stranded polynucleotide; wherein the pharmaceutically acceptable carrier is selected from the group consisting of a physiological solution, liposomes, and a composition which facilitates entry of the FasL sense and FasL antisense polynucleotides into cells upon intratumoral administration of the pharmaceutical composition; and wherein the FasL sense polynucleotide is operatively linked to a promoter for expression and the FasL antisense polynucleotide is operatively linked to a promoter for expression.

* * * * *

SEQUENCE LISTING

<160> NUMBER OF SEQ ID NOS: 8

<210> SEQ ID NO 1
<211> LENGTH: 972

-continued

```
<212> TYPE: DNA
<213> ORGANISM: Homo sapiens

<400> SEQUENCE: 1
tctagactca ggactgagaa gaagtaaaac cgtttgctgg ggctggcctg          50
actcaccagc tgcc atg cag cag ccc ttc aat tac cca tat ccc         94 cag atc tac tgg gtg gac agc agt gcc agc tct ccc tgg gcc        136 cct cca ggc aca gtt ctt ccc tgt cca acc tct gtg ccc aga        178 agg cct ggt caa agg agg cca cca cca cca ccg cca ccg cca        220 cca cta cca cct ccg ccg ccg cca cca ctg cct cca cta            262 ccg ctg cca ccc ctg aag aag aga ggg aac cac agc aca ggc        304 ctg tgt ctc ctt gtg atg ttt ttc atg gtt ctg gtt gcc ttg        346 gta gga ttg ggc ctg ggg atg ttt cag ctc ttc cac cta cag        388 aag gag ctg gca gaa ctc cga gag tct acc agc cag atg cac        430 aca gca tca tct ttg gag aag caa ata ggc cac ccc agt cca        472 ccc cct gaa aaa aag gag ctg agg aaa gtg gcc cat tta aca        514 ggc aag tcc aac tca agg tcc atg cct ctg gaa tgg gaa gac        556 acc tat gga att gtc ctg ctt tct gga gtg aag tat aag aag        598 ggt ggc ctt gtg atc aat gaa act ggg ctg tac ttt gta tat        640 tcc aaa gta tac ttc cgg ggt caa tct tgc aac aac ctg ccc        682 ctg agc cac aag gtc tac atg agg aac tct aag tat ccc cag        724 gat ctg gtg atg atg gag ggg aag atg atg agc tac tgc act        766 act ggg cag atg tgg gcc cgc agc agc tac ctg ggg gca gtg        808 ttc aat ctt acc agt gct gat cat tta tat gtc aac gta tct        850 gag ctc cct ctg gtc aat ttt gag gaa tct cag acg ttt ttc        892 ggc tta tat aag ctc taagagaagc actttgggat tctttccatt           937
atgattcttt gttacaggca ccgagatgtt ctaga                         972

<210> SEQ ID NO 2
<211> LENGTH: 940
<212> TYPE: DNA
<213> ORGANISM: murine

<400> SEQUENCE: 2
gctctagaga aggaaaccct ttcctggggc tgggtgcc atg cag cag            47 ccc atg aat tac cca tgt ccc cag atc ttc tgg gta gac agc         89 agt gcc act tca tct tgg gct cct cca ggg tca gtt ttt ccc        131 tgt cca tct tgt ggg cct aga ggg ccg gac caa agg aga ccg        173 cca cct cca cca cca cct gtg tca cca cta cca ccg cca tca        215 caa cca ctc cca ctg ccg cca ctg acc cct cta aag aag aag        257 gac cac aac aca aat ctg tgg cta ccg gtg gta ttt ttc atg        299 gtt ctg gtg gct ctg gtt gga atg gga tta gga atg tat cag        341 ctc ttc cac ctg cag aag gaa ctg gca gaa ctc cgt gag ttc        383 acc aac caa agc ctt aaa gta tca tct ttt gaa aag caa ata        425
```

```
gcc aac ccc agt aca ccc tct gaa aaa aaa gag ccg agg agt         467 gtg gcc cat tta aca ggg aac ccc cac tca agg tcc atc cct         509 ctg gaa tgg gaa gac aca tat gga acc gct ctg atc tct gga         551 gtg aag tat aag aaa ggt ggc ctt gtg atc aac gaa act ggg         593 ttg tac ttc gtg tat tcc aaa gta tac ttc cgg ggt cag tct         635 tgc aac aac cag ccc cta aac cac aag gtc tat atg agg aac         677 tct aag tat cct gag gat ctg gtg cta atg gag gag aag agg         719 ttg aac tac tgc act act ggc cag ata tgg gcc cac agc agc         761 tac ctg ggg gca gta ttc aat ctt acc agt gct gac cat tta         803 tat gtc aac ata tct caa ctc tct ctg atc aat ttt gag gaa         845 tct aag acc ttt ttc ggc ttg tat aag ctt taaaagaaaa              885 agcattttaa aatgatctac tattctttat catgggcacc aggaatatct          935
agagc                                                           940
```

<210> SEQ ID NO 3
<211> LENGTH: 281
<212> TYPE: PRT
<213> ORGANISM: Homo sapiens

<400> SEQUENCE: 3

```
Met Gln Gln Pro Phe Asn Tyr Pro Tyr Pro Gln Ile Tyr Trp Val Asp
1               5                   10                  15

Ser Ser Ala Ser Pro Trp Ala Pro Pro Gly Thr Val Leu Pro Cys
            20                  25                  30

Pro Thr Ser Val Pro Arg Arg Pro Gly Gln Arg Arg Pro Pro Pro
            35                  40                  45

Pro Pro Pro Pro Pro Leu Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240
```

```
Arg Ser Ser Tyr Leu Gly Ala Val Phe Asn Leu Thr Ser Ala Asp His
            245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
            275                 280

<210> SEQ ID NO 4
<211> LENGTH: 23
<212> TYPE: DNA
<213> ORGANISM: Artificial
<220> FEATURE:
<221> NAME/KEY:
<222> LOCATION:
<223> OTHER INFORMATION: synthesized

<400> SEQUENCE: 4
tctactggcg ctgccaaggc tgt                                         23

<210> SEQ ID NO 5
<211> LENGTH: 22
<212> TYPE: DNA
<213> ORGANISM: Artificial
<220> FEATURE:
<221> NAME/KEY:
<222> LOCATION:
<223> OTHER INFORMATION: synthesized

<400> SEQUENCE: 5
acagggtggt ggacctcatg gc                                          22

<210> SEQ ID NO 6
<211> LENGTH: 16
<212> TYPE: DNA
<213> ORGANISM: Artificial
<220> FEATURE:
<221> NAME/KEY:
<222> LOCATION:
<223> OTHER INFORMATION: synthesized

<400> SEQUENCE: 6
aagtgagtgg gtgttt                                                 16

<210> SEQ ID NO 7
<211> LENGTH: 972
<212> TYPE: DNA
<213> ORGANISM: Homo sapiens

<400> SEQUENCE: 7
tctagaacat ctcggtgcct gtaacaaaga atcataatgg aaagaatccc            50
aaagtgcttc tcttagagct tatataagcc gaaaaacgtc tgagattcct            100
caaaattgac cagagagagc tcagatacgt tgacatataa atgatcagca            150
ctggtaagat tgaacactgc ccccaggtag ctgctgcggg cccacatctg            200
cccagtagtg cagtagctca tcatcttccc ctccatcatc accagatcct            250
ggggatactt agagttcctc atgtagacct tgtggctcag gggcaggttg            300
ttgcaagatt gaccccggaa gtatactttg aatatacaa agtacagccc             350 agtttcattg atcacaaggc acccttctt atacttcact ccagaaagca             400
ggacaattcc ataggtgtct tcccattcca gaggcatgga ccttgagttg            450
gacttgcctg ttaaatgggc cactttcctc agctcctttt tttcaggggg            500
```

-continued

```
tggactgggg tggcctattt gcttctccaa agatgatgct gtgtgcatct        550
ggctggtaga ctctcggagt tctgccagct ccttctgtag gtggaagagc        600
tgaaacatcc ccaggcccaa tcctaccaag gcaaccagaa ccatgaaaaa        650
catcacaagg agacacaggc ctgtgctgtg gttccctctc ttcttcaggg        700
gtggcagcgg tagtggaggc agtggtggcg gcggcggcgg aggtggtagt        750
ggtggcggtg gcggtggtgg tggtggcctc ctttgaccag gccttctggg        800
cacagaggtt ggacagggaa gaactgtgcc tggaggggcc cagggagagc        850
tggcactgct gtccacccag tagatctggg gatatgggta attgaagggc        900
tgctgcatgg cagctggtga gtcaggccag ccccagcaaa cggttttact        950
tcttctcagt cctgagtcta ga                                      972

<210> SEQ ID NO 8
<211> LENGTH: 940
<212> TYPE: DNA
<213> ORGANISM: murine

<400> SEQUENCE: 8
gctctagata ttcctggtgc ccatgataaa gaatagtaga tcattttaaa         50
atgctttttc ttttaaagct tatacaagcc gaaaaaggtc ttagattcct        100
caaaattgat cagagagagt tgagatatgt tgacatataa atggtcagca        150
ctggtaagat tgaatactgc ccccaggtag ctgctgtggg cccatatctg        200
gccagtagtg cagtagttca acctcttctc ctccattagc accagatcct        250
caggatactt agagttcctc atatagacct tgtggtttag gggctggttg        300
ttgcaagact gaccccggaa gtatactttg gaatacacga agtacaaccc        350
agtttcgttg atcacaaggc cacctttctt atacttcact ccagagatca        400
gagcggttcc atatgtgtct tcccattcca gagggatgga ccttgagtgg        450
gggttccctg ttaaatgggc cacactcctc ggctcttttt tttcagaggg        500
tgtactgggg ttggctattt gcttttcaaa agatgatact ttaaggcttt        550
ggttggtgaa ctcacggagt tctgccagtt ccttctgcag gtggaagagc        600
tgatacattc ctaatcccat tccaaccaga gccaccagaa ccatgaaaaa        650
taccaccggt agccacagat ttgtgttgtg gtccttcttc tttagagggg        700
tcagtggcgg cagtgggagt ggttgtgatg gcggtggtag tggtgacaca        750
ggtggtggtg gaggtggcgg tctcctttgg tccggccctc taggcccaca        800
agatggacag ggaaaaactg accctggagg agcccaagat gaagtggcac        850
tgctgtctac ccagaagatc tggggacatg ggtaattcat gggctgctgc        900
atggcaccca gccccaggaa agggtttcct tctctagagc                   940
```